United States Patent [19]

Shea

[11] Patent Number: 5,713,839
[45] Date of Patent: Feb. 3, 1998

[54] PRE-OPERATIVE NASAL SPLINT FOR ENDOSCOPIC SINUS SURGERY

[76] Inventor: John P. Shea, 232 SW. Brushy Mound, Burleson, Tex. 76028

[21] Appl. No.: 723,112

[22] Filed: Sep. 30, 1996

Related U.S. Application Data

[62] Division of Ser. No. 557,680, Nov. 13, 1995, Pat. No. 5,599,284, which is a continuation of Ser. No. 385,567, Feb. 8, 1995, abandoned.

[51] Int. Cl.⁶ ........................................... A61F 5/00
[52] U.S. Cl. .................. 602/17; 602/5; 606/196; 606/199
[58] Field of Search ..................... 606/196, 199, 606/201, 204, 204.45, 232; 602/5, 6, 17; 128/858, 898, 201.18

[56] References Cited

U.S. PATENT DOCUMENTS

| | | |
|---|---|---|
| 3,935,859 | 2/1976 | Doyle . |
| 4,402,314 | 9/1983 | Goode . |
| 4,592,357 | 6/1986 | Ersek . |
| 4,646,739 | 3/1987 | Doyle . |
| 5,024,658 | 6/1991 | Koslov . |
| 5,094,233 | 3/1992 | Brennan . |
| 5,350,396 | 9/1994 | Eliachar . |

*Primary Examiner*—Richard J. Apley
*Assistant Examiner*—Victor K. Hwang
*Attorney, Agent, or Firm*—James E. Bradley

[57] ABSTRACT

A nasal splint comprising a turbinate retaining portion and securing system for securing the splint against the nasal septum and causing the turbinate retaining portion of the splint to retain the middle turbinate against the nasal septum. In operation, the nasal splint is placed inside the nose prior to performing endoscopic surgery. The splint is secured to the nasal septum so as to retain the middle turbinate against the nasal septum. Endoscopic surgery is then performed while still retaining the middle turbinate against the nasal septum.

11 Claims, 2 Drawing Sheets

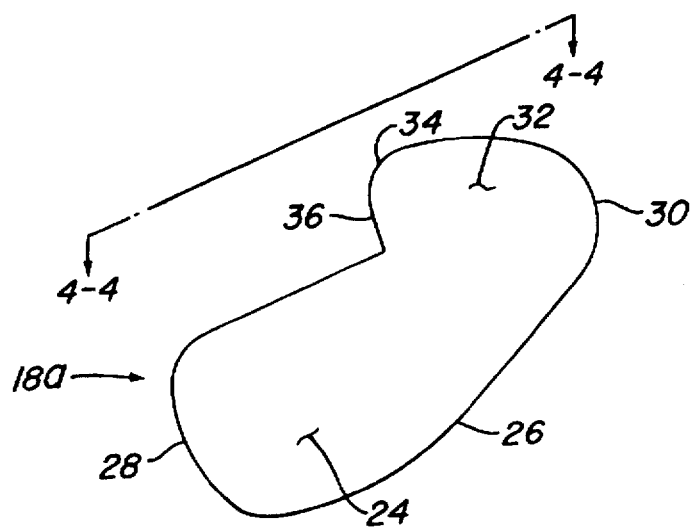
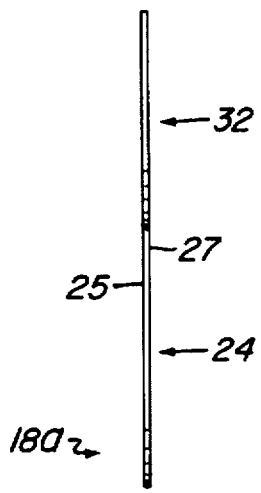
Fig. 3  Fig. 4
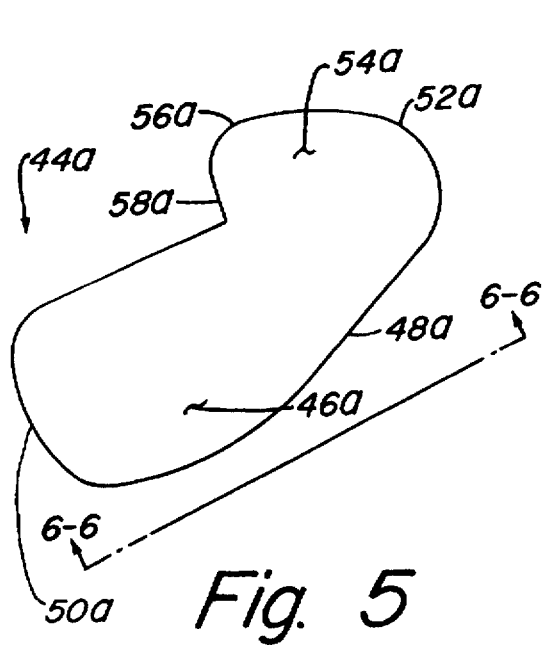
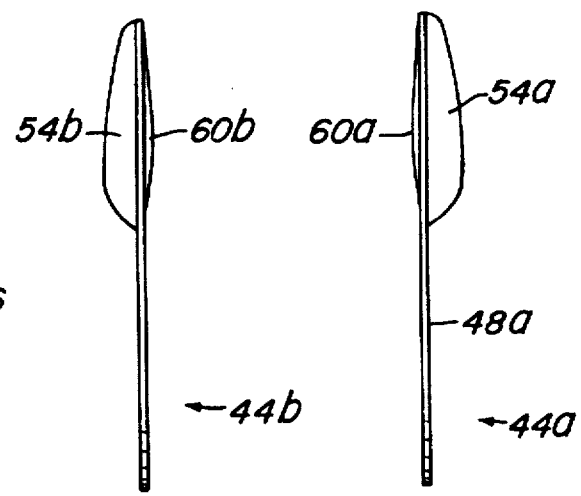
Fig. 5  Fig. 7  Fig. 6

5,713,839

PRE-OPERATIVE NASAL SPLINT FOR ENDOSCOPIC SINUS SURGERY

This is a division of application Ser. No. 08/557,680, filed Nov. 13, 1995, U.S. Pat. No. 5,599,284, which in turn is a continuation of application Ser. No. 08/385,567, filed Feb. 8, 1995, now abandoned.

BACKGROUND OF THE INVENTION

1. Field of the Invention

This invention relates in general to nasal splints, and in particular to nasal splints used before nasal endoscopic surgery to retain the middle turbinate against the nasal septum.

2. Description of the Prior Art

Nasal splints are commonly used as nasal post-operative devices. A variety of such splints are available to address particular problems encountered after nasal septal reconstructive surgery. For example, after nasal septal reconstructive surgery, splints are often used to support the septum in the proper orientation to allow the septum to heal properly. Some splints have means to facilitate breathing or nasal drainage. Other splints have means for reducing crusting or adhesion of the nasal splint to the septum.

Some splints are also available for use after nasal endoscopic surgery. In some types of nasal endoscopic surgery, transection of the middle turbinate is necessary, later resulting in adhesion problems with the septum or lateral nasal wall. Splints are available to maintain the middle turbinate separated from the septum and lateral nasal wall to avoid adhesion.

Thus, the currently available nasal splints are generally used as post operative devices to maintain the reconstructed nasal structures in proper orientation, or to isolate the various nasal structures so as to avoid adhesion.

However, the currently available splints do not solve a lot of the problems associated with nasal endoscopic surgery. Because the middle turbinate obstructs the entrance to the sinus passages, the middle turbinates have to be pushed aside to obtain visualization of the sinus passages so that endoscopic tools can be inserted therein. Having to hold the middle turbinate out of the way adds to the tasks which the surgeon must perform, thus detracting from the attention the surgeon can give to the other tasks he or she must perform. Additionally, while the endoscopic tools are being inserted and removed from the sinus passages, the middle turbinate tends to return to its natural position, thus leaning against the tools. The rubbing of the endoscopic tools against the middle turbinate often results in injury to the middle turbinate, which can cause post operative discomfort for the patient, infection, and other complications.

The need exists for a pre-operative device for increasing visualization of the nasal cavities so as to facilitate nasal endoscopic surgery. A need also exists for a device that protects the middle turbinate from being injured by the movement of the endoscopic tools during nasal endoscopic surgery.

SUMMARY OF THE INVENTION

It is the general object of the invention to provide a pre-operative device which increases visualization of the nasal cavities so as to facilitate nasal endoscopic surgery. It is another object of the present invention to provide a device that protects the middle turbinate from being injured by the movement of the endoscopic tools during nasal endoscopic surgery.

The apparatus of the present invention is a pre-operative nasal splint comprising a turbinate retaining portion and a securing means for securing the splint against the nasal septum and causing the turbinate retaining portion of the splint to retain the middle turbinate against the nasal septum. In operation, the splint of the present invention is placed inside the nose prior to performing endoscopic surgery. The splint retains the middle turbinate against the nasal septum by securing the splint to the nasal septum. Endoscopic surgery is then performed while still retaining the middle turbinate against the nasal septum.

The above as well as additional objects, features, and advantages will become apparent in the following description.

BRIEF DESCRIPTION OF THE DRAWINGS

FIG. 3 is a side view illustrating a first embodiment of the nasal splint of the present invention for use in the left nasal cavity of a patient.

FIG. 4 is a view of the nasal splint of FIG. 3 taken along line 4—4 of FIG. 3.

FIG. 5 is a side view illustrating a second embodiment of the nasal splint of the present invention for use in the left nasal cavity.

FIG. 6 is a view of the nasal splint of FIG. 5, taken along line 6—6 of FIG. 5.

FIG. 7 is a view similar to FIG. 6 but illustrating a splint according to the second embodiment for use in the right nasal cavity.

DETAILED DESCRIPTION OF THE INVENTION

Figure 1:
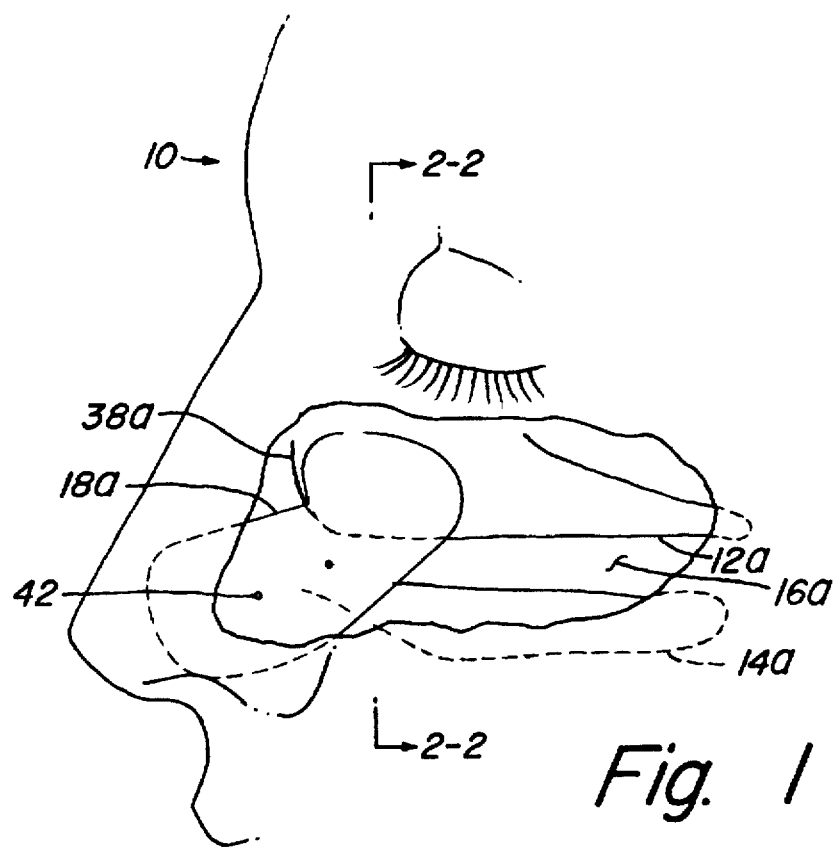
FIG. 1 is a side cut-a-way view of a human face, with the cut-a-way showing the nasal splint according to the present invention holding the middle turbinate of the left nasal cavity against the nasal septum.

FIG. 1 shows a side cut-a-way view of the left portion of the head 10 of a patient. The left middle turbinate 12a is located within the left nasal cavity 16a. The left lower turbinate 14a is also located within nasal cavity 16a. The nasal splint 18a of the present invention is also shown located in the left nasal cavity 16a.

Figure 2:
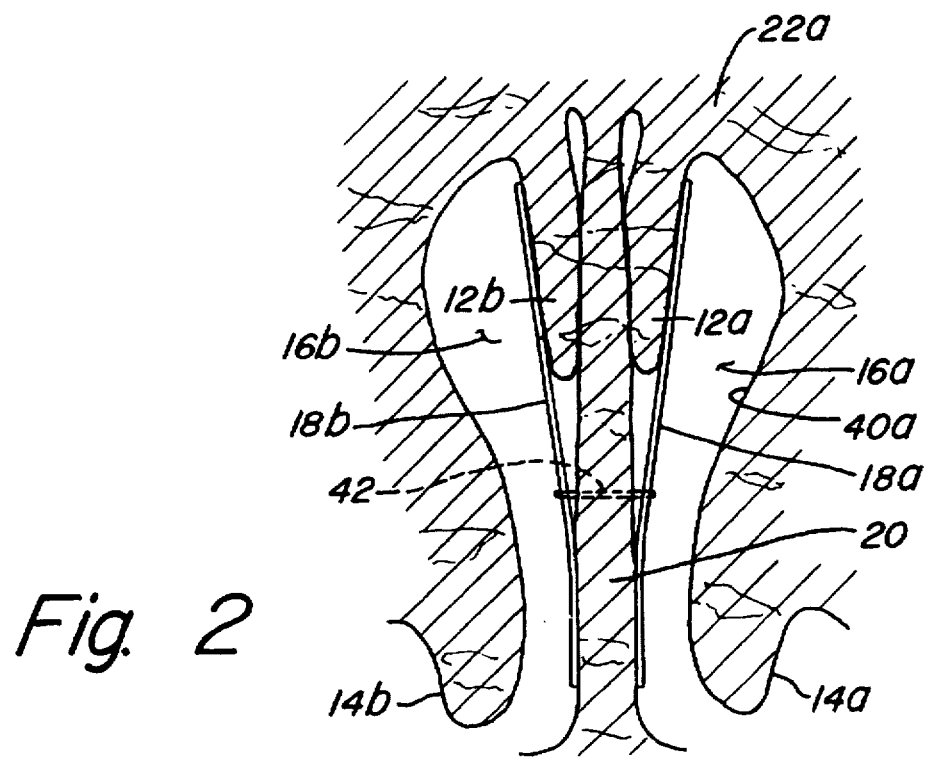
FIG. 2 is a cross sectional view taken along line 2—2 of FIG. 1 and depicting the middle turbinates being retained against the nasal septum by nasal splints according to the present invention.

FIG. 2 shows a cross sectional view of the left and right nasal cavities 16a, 16b taken along line 2—2 of FIG. 1. The left middle turbinate 12a and the left lower turbinate 14a are located in the left nasal cavity 16a. The right middle turbinate 12b and right lower turbinate 14b are located in the right nasal cavity 16b. The right and left nasal cavities 16a, 16b are separated by the nasal septum 20.

For purposes of brevity and simplicity, the detailed description of the present invention will describe in detail only the splint for use in the left nasal cavity 16a, the splint for the right nasal cavity 16b being merely a mirror image of the splint for the left nasal cavity 16a.

The middle turbinate 12a depends from the upper portion 22a of nasal cavity 16a. Although in FIG. 2 middle turbinate 12a is shown retained against septum 20 by splint 18a, when unrestrained, middle turbinate 12a hangs toward the central portion of nasal cavity 16a. When middle turbinate 12a is in the unrestrained position, it obstructs visualization of, and access to, the sinus passages (not shown). The splint 18a of the present invention is used prior to nasal endoscopic surgery to retain the middle turbinate 12a against the nasal septum 20, as described in more detail below.

Referring now to FIGS. 3 and 4, a splint 18a according to the present invention is shown. Splint 18a comprises a substantially flat, elongate body 24 having two substantially flat surfaces 25, 27. Body 24 has an arcuate lower edge 26. Lower edge 26 terminates into two arcuate side edges 28, 30. Side edge 30 is smaller than side edge 28 because it is designed to be placed deeper into nasal cavity 16a, and must be smaller to fit therein. A turbinate retaining portion 32 extends upwardly from body 24 to form a tab which extends upwardly from body 24. Turbinate retaining portion 32 and body 24 form an upper edge 34 of splint 18a having a concave notch 36 therein. The anterior aspect 38a of the middle turbinate 12a is connected to the nasal cavity wall 40a. Notch 36 is shaped so as to conform to the anterior aspect 38a of the middle turbinate 12a where middle turbinate 12a is connected to the nasal cavity wall 40a. Notch 36 prevents splint 18a from applying excessive pressure on middle turbinate 12a and thus lessens the chance for post-operative pain in this area. The remainder of turbinate retaining portion 32 is shaped to fit between middle turbinate 12a and nasal cavity wall 40a.

Referring now to FIGS. 1-4, in operation, splint 18a of the present invention functions as follows. When and if indicated, nasal septal reconstruction is performed and the lateral aspect of the middle turbinate concha bullosa, polyp, or bony abnormality is removed. In the cases where the patient has a straight and thin septum, septal reconstruction is not necessary and can be avoided.

Splint 18a is inserted into nasal cavity 16a with side edge 30 entering nasal cavity 16a first, and with the turbinate retaining portion, or tab 32 oriented upwardly. Splint 18a is placed laterally to, and exteriorly of, the middle turbinate 12a so that middle turbinate 12a is sandwiched between nasal septum 20 and splint 18a. The notch 36 formed in the upper edge 34 of splint 18a conforms to the anterior aspect 38a of the middle turbinate 12a, as described above.

A securing means 42 secures splint 18a against septum 20. In the present embodiment securing means 42 is a transseptal suture which secures splint 18a to septum 20, and splint 18b located on the opposite side of septum 20. Once the suture is in place, suture tension and splint placement are checked.

Once splint 18a is in place, it retains middle turbinate 12a against nasal septum 20, thus providing visualization of the sinus passages. The sinus endoscope and other tools and instrumentation can be more easily inserted into the sinus passages without causing instrumentation trauma of the middle turbinate. Also, the erectile portion of the anterior nasal septum is compressed and kept from the surgical field as well. After the nasal endoscopic surgery is complete, a pack moistened with antibiotic can be placed in the middle meatus, lateral to the splint.

A splint 18b is similarly used in the right nasal cavity 16a. Splint 18b would be a mirror image of splint 18a.

Referring now to FIGS. 5 and 6, a splint 44a according to a second embodiment of the present invention, and for use in the left nasal cavity 16a, is shown. Like splint 18a, splint 44a also has a substantially flat and elongate body 46a. Also like splint 18a, splint 44a has a lower edge 48a and side edges 50a, 52a. A turbinate retaining portion 54a extends upwardly from body 46a to form a tab which extends upwardly from body 46a. Turbinate retaining portion 54a and body 46a form an upper edge 56a of splint 44a having a concave notch 58a therein. Notch 58a is shaped so as to conform to, or "hook" around, the anterior aspect 38a of middle turbinate 12a where middle turbinate 12a is connected to the nasal cavity wall 40a.

The difference between splint 44a and splint 18a is that the turbinate retaining portion 54a of splint 44a has a slight "cupped" shape, or cup 60a which is convex in shape as seen from nasal cavity 16a and concave in shape as seen from middle turbinate 12a. Cup 60a helps to better retain middle turbinate 12a against the nasal septum 20.

Referring now to FIG. 7, a splint 44b according to the second embodiment of the present invention and for use in the right nasal cavity 16b is shown. Splint 44b is the mirror image of splint 44a. The turbinate retaining portion 54b of splint 44b has a slight "cupped" shape, or cup 60b which is convex in shape as seen from nasal cavity 16b and concave in shape as seen from middle turbinate 12b. Cup 60b helps to better retain middle turbinate 12b against the nasal septum 20.

The splints of the above embodiments are preferably made of a synthetic resin polymer such as the material sold under the trademark TEFLON having a thickness of about 0.5 millimeters. Although different thicknesses can be used, this thickness has been found to provide sufficient stiffness while allowing more clearance for endoscopic tools during surgery and for post-operative care.

Other materials, such as plastic can also be used if a stiffer splint is desired. However, the preferred material is Teflon because it gives the splint a certain degree of malleability. The malleable nature of the splint allows the surgeon to conform the splint to the anatomic variations of the turbinate and septum. Thus, a surgeon can start with the flat splint 18a of FIGS. 3 and 4, or with the pre-shaped splint 44a of FIGS. 5 and 6, and modify them as needed to better fit the particular anatomic variations of the turbinate and septum of the particular patient.

The nasal splint of the present invention provides considerable advantages over the currently available methods and apparatuses for performing nasal endoscopic surgery. Using the splint of the present invention prior to endoscopic sinus surgery improves visualization of the sinus passages during surgery. The pre-operative use of the splint of the present invention also avoids instrumentation trauma of the middle turbinate caused by instruments rubbing against the middle turbinate during surgery. Thus, the splint of the present invention solves the problem of the "floppy turbinate" well known to persons skilled in the art. Surgery is made easier, safer, and quicker.

The splint of the present invention also avoids the need for "staging" the endoscopic sinus surgery after nasal septal reconstruction. Post-operative care is also improved, eliminating scarring and lateralisation of the middle turbinate, and facilitating nasal cleansing, both by patient and physician.

Still further, the malleable nature of the splint of the present invention provides the additional advantage of allowing the surgeon to conform the splint to the anatomic variation of the turbinate and septum of each patient.

While the invention has been particularly shown and described with reference to a preferred embodiment, it will be understood by those skilled in the art that various changes in form and detail may be made therein without departing from the spirit and scope of the invention.

What is claimed is:

1. An improved nasal splint for use in a human nose having a nasal septum and a middle turbinate with an anterior aspect, the improvement comprising:

a thin body having two substantially flat sides;

the sides of the body being free of protruberances;

a substantially flat turbinate retaining portion integrally formed with the body so as to form the splint;

a notch located on an upper edge of the splint, the notch being shaped and configured to conform to the anterior aspect of the middle turbinate; and securing means for securing the splint to the nasal septum so that the body of the splint mates with the nasal septum and the turbinate retaining portion mates with the middle turbinate and causing the splint to retain the middle turbinate against the nasal septum.

2. The nasal splint according to claim 1 wherein the securing means comprises a transseptal suture.

3. The nasal splint according to claim 1 wherein the securing means comprises a transseptal suture and wherein the splint has two holes therethrough for placement of the suture.

4. The nasal splint according to claim 1 wherein the splint is made of teflon.

5. The nasal splint according to claim 1 wherein the splint is malleable to allow shaping of the splint to better conform to the shape of the middle turbinate.

6. An improved nasal splint for use in a nose having a nasal septum and a middle turbinate, the improved nasal splint comprising in combination:

a substantially flat body having inward and outward facing surfaces;

the inward and outward facing surfaces of the body being free of any protruberances;

a substantially flat turbinate retaining portion having inward and outward facing surfaces;

the inward and outward facing surfaces of the turbinate retaining portion being free of any protuberances;

the inward facing surfaces of the turbinate retaining portion being adapted to mate with an outer surface of the middle turbinate;

the body and the turbinate retaining portion being integrally formed;

securing means for securing the splint to the nasal septum so that the inward facing surface of the body of the splint mates with the nasal septum and the inward facing surface of the turbinate retaining portion mates with the middle turbinate thus causing the splint to retain the middle turbinate against the nasal septum; and the splint having an upper edge and the splint further comprising a concave notch in the upper edge shaped to conform to an anterior aspect of the middle turbinate.

7. An improved nasal splint for use in a nose having a nasal septum and a middle turbinate with an anterior aspect, the improvement comprising:

a thin body having two substantially flat sides;

the sides of the body being free of protruberances;

a substantially flat turbinate retaining portion having a cupped shape to better retain the middle turbinate;

the turbinate retaining portion being free of protuberances;

the body and turbinate retaining portion being integrally formed;

a notch located on an upper edge of the splint, the notch being shaped and configured to conform to the anterior aspect of the middle turbinate;

securing means for securing the splint against the nasal septum so that the turbinate retaining portion of the splint retains the middle turbinate against the nasal septum.

8. The nasal splint according to claim 7 wherein the securing means comprises a transseptal suture.

9. The nasal splint according to claim 7 wherein the securing means comprises a transseptal suture and wherein the splint has two holes therethrough for placement of the suture.

10. The nasal splint according to claim 7 wherein the splint is made of teflon.

11. The nasal splint according to claim 7 wherein the splint is malleable to allow shaping of the splint to better conform to the shape of the middle turbinate.

* * * * *